(12) United States Patent
Feng et al.

(10) Patent No.: US 10,813,551 B2
(45) Date of Patent: Oct. 27, 2020

(54) PROBE AND MANUFACTURING METHOD THEREOF

(71) Applicant: BEIJING SMTP TECHNOLOGY CO., LTD., Beijing (CN)

(72) Inventors: Zhen Feng, Beijing (CN); Qun Cao, Beijing (CN)

(73) Assignee: BEIJING SMTP TECHNOLOGY CO., LTD., Beijing (CN)

( * ) Notice: Subject to any disclaimer, the term of this patent is extended or adjusted under 35 U.S.C. 154(b) by 115 days.

(21) Appl. No.: 16/202,243

(22) Filed: Nov. 28, 2018

(65) Prior Publication Data

US 2019/0090917 A1 Mar. 28, 2019

Related U.S. Application Data

(63) Continuation of application No. PCT/CN2017/085163, filed on May 19, 2017.

(51) Int. Cl.
*A61B 5/00* (2006.01)
*A61B 17/70* (2006.01)
(Continued)

(52) U.S. Cl.
CPC .............. *A61B 5/00* (2013.01); *A61B 5/053* (2013.01); *A61B 17/7082* (2013.01);
(Continued)

(58) Field of Classification Search
CPC ............................. A61B 17/7082; A61B 5/00
See application file for complete search history.

(56) References Cited

U.S. PATENT DOCUMENTS 6,391,005 B1 5/2002 Lum et al.
7,580,743 B2 * 8/2009 Bourlion ............... A61B 5/0538
600/547
(Continued)

FOREIGN PATENT DOCUMENTS

CN 1827041 A 9/2006
CN 101295851 A 10/2008
(Continued)

OTHER PUBLICATIONS

Machine translation of CN 101295851, retrieved from https://patents.google.com on Jun. 19, 2020 (Year: 2020).*

(Continued)

*Primary Examiner* — Christian A Sevilla
(74) *Attorney, Agent, or Firm* — Thomas E. Lees, LLC (57) ABSTRACT

The invention discloses a probe and a method of manufacturing the same. The probe has a long cylindrical shape and includes a probe head (1), a probe body (2) at the rear of the probe head (1), and a probe tail (3) at a rear end of the probe body (2). The probe has a three-layer composite structure. The probe tail is a three-layer composite structure. The probe of the invention is used to detect a body tissue, and according to different electrical signals fed back by different body tissues, a type of the body tissue being detected by the probe can be known, thereby avoiding a medical accident in which a spinal cord or nerve is injured by a screw intruded into a vertebral foramen. The probe of the invention is simple in structure, convenient for use, easy in operation, of high reliability, high surgical safety and high success rate of surgery.

11 Claims, 7 Drawing Sheets (51) Int. Cl.

| | |
|---|---|
| *A61B 5/053* | (2006.01) |
| *A61B 17/88* | (2006.01) |
| *A61B 17/92* | (2006.01) |
| *B29C 45/00* | (2006.01) |
| *B29C 45/14* | (2006.01) |
| *B29C 45/17* | (2006.01) |
| *A61B 17/00* | (2006.01) |
| *B29K 705/00* | (2006.01) |
| *B29L 31/00* | (2006.01) |

(52) U.S. Cl.
CPC .............. *A61B 17/88* (2013.01); *A61B 17/92* (2013.01); *B29C 45/0053* (2013.01); *B29C 45/14467* (2013.01); *B29C 45/1753* (2013.01); *A61B 2017/00526* (2013.01); *B29K 2705/00* (2013.01); *B29K 2995/0007* (2013.01); *B29L 2031/752* (2013.01)

(56) References Cited

U.S. PATENT DOCUMENTS

| | | | |
|---|---|---|---|
| 9,538,935 B2* | 1/2017 | Bourlion | A61B 17/6491 |
| 2002/0161312 A1* | 10/2002 | Campbell | A61B 5/0531 600/547 |
| 2003/0088186 A1* | 5/2003 | Doody | A61B 5/053 600/547 |
| 2005/0107718 A1 | 5/2005 | Hashimshony | |
| 2006/0276721 A1* | 12/2006 | McGinnis | A61B 17/1626 600/547 |
| 2008/0167659 A1 | 7/2008 | Bourlion et al. | |
| 2012/0035607 A1* | 2/2012 | Karwei | A61B 17/320016 606/46 |
| 2012/0089123 A1 | 4/2012 | Organ et al. | |
| 2013/0296734 A1 | 11/2013 | Bourlion et al. | |

FOREIGN PATENT DOCUMENTS

| | | | |
|---|---|---|---|
| CN | 101832482 A | | 9/2010 |
| CN | 101884565 A | | 11/2010 |
| CN | 201918433 U | | 8/2011 |
| CN | 103327893 A | | 9/2013 |
| CN | 104287821 A | | 1/2015 |
| CN | 204708972 U | | 10/2015 |
| CN | 106073704 | * 11/2016 | ............... A61B 5/00 |
| CN | 106073704 A | | 11/2016 |
| WO | 2013172869 A1 | | 11/2013 |

OTHER PUBLICATIONS

Machine translation of CN 103327893, retrieved from https://patents.google.com on Jun. 19, 2020 (Year: 2020).*
Machine translation of CN 201918433, retrieved from https://patents.google.com on Jun. 19, 2020 (Year: 2020).*
Machine translation of CN 101832482, retrieved from https://patents.google.com on Jun. 19, 2020 (Year: 2020).*
European Search Report for European Patent Application No. 17805686.7; European Patent Office; Munich, Germany; dated Jun. 5, 2020.
European Partial Supplementary European Search Report for European Patent Application No. 17805686.7; European Patent Office; Munich, Germany; dated Jan. 27, 2020.
Chinese Search Report for Chinese Patent Application No. 201610373500.9; Chinese Patent Office; dated Jun. 13, 2018.
Chinese Office Action for Chinese Patent Application No. 201610373500.9; Chinese Patent Office; dated Jun. 28, 2018.
Chinese Office Action for Chinese Patent Application No. 201610373500.9; Chinese Patent Office; dated Apr. 9, 2019.
Chinese Office Action for Chinese Patent Application No. 201610373500.9; Chinese Patent Office; dated Oct. 12, 2019.
Bian-jun; "Plastic Moldling Principles and Processes"; Lin Highland editor; ISBN: 978-7-5643-4199-2; Chengdu: Southwest Jiaotong University Press; 2015.
International Search Report for PCT Application No. PCT/CN2017/085163; State Intellectual Property Office of P.R. China; Beijing, China; dated Jul. 28, 2017.
Written Opinion of the International Searching Authority for PCT Application No. PCT/CN2017/085163; State Intellectual Property Office of the P.R. China; Beijing, China; dated Jul. 28, 2017.
Translation of the International Search Report for PCT Application No. PCT/CN2017/085163; State Intellectual Property Office of the P.R. China; Beijing, China; dated Jul. 28, 2017.
English Translation of the Written Opinion of the International Searching Authority for PCT Application No. PCT/CN2017/085163; International Searching Authority; dated Jul. 28, 2017.

* cited by examiner

PROBE AND MANUFACTURING METHOD THEREOF

CROSS REFERENCE TO RELATED APPLICATIONS

This is a Continuation application of International Application Serial No. PCT/CN2017/085163, filed May 19, 2017, which claims the benefit of Chinese Application No. 201610373500.9, filed May 31, 2016, the disclosures of which are hereby incorporated by reference.

BACKGROUND

The present disclosure relates to the field of medical devices, and in particular to a probe and a method of manufacturing the same.

In the long-term production activities, human beings have gradually developed a skeletal structure suitable for upright walking and labor. However, with the improvement of industrial technology in recent years, the development of mechanical equipment has gradually freed human beings from physical labor. People sit at a desk and before a computer more and more, engaging in production and operation indoors. This seemingly progressive work style has invisibly deprived people of the right to work physically and the opportunities for physical exercise. More and more people are suffering from spinal diseases such as lumbar disc herniation, Lamina inflammation, scoliosis and so on. To this end, spinal surgery has become a common surgical procedure along with the industrialization process.

When performing spinal surgery and neurosurgery operation, it is usually necessary to perform operations such as cutting and drilling a lamina. It is known to those who have some knowledge of Structure of Spine that the lamina is a bone plate that connects a vertebral arch, a vertebral body, anterior and posterior articular processes, a transverse process, and a nerve spine, and is located at a junction of Spine. After an operation of laminectomy, a screw or other fastening member must be let into the vertebral body from the pedicle root so as to fix Spine, otherwise the function of the patient's spine will be seriously affected.

In the human body, a vertebral foramen surrounding Spinal cord is formed between the posterior side of the lamina and the vertebral body, and Spinal cord and nerves pass through the vertebral foramen. Care must be taken in spinal surgery. A little carelessness during surgery can cause damage to Spinal cord and nerves and cause permanent damage to the patient. Therefore, performing a vertebral plate fixation surgery is a very difficult operation. The more unfavorable situation is that due to Special structure of Spine, the medical staff can not observe the penetration of Screw from the outside, and the operation relies almost entirely on the doctor's surgical experience. If Screw is deflected into the vertebral foramen, the hard screw head is likely to cause irreparable damage to Spinal cord or nerves in the vertebral foramen, causing a serious medical accident. Therefore, the risk of surgical operation is extremely high, the dependence on the doctor's operation level is extremely high, and Success rate of surgery is low.

BRIEF SUMMARY

In order to solve the above problems, a first aspect of the present invention provides a probe having a long cylindrical shape and including a probe head, a probe body at a rear end of the probe head, and a probe tail at a rear end of the probe body. The probe has a three-layer composite structure, an outermost layer of the probe is an outer conductive shell, an innermost layer of the probe is an inner conductive rod, and an insulating layer is disposed between the outer conductive shell and the inner conductive rod.

According to an embodiment of the probe of the present invention, preferably, an outer diameter of the probe head is smaller than that of the probe body, an outer surface of the probe head is smoothly connected to an outer surface of the probe body, a front end of the probe head is of a conical structure, and the inner conductive rod protrudes from the conical structure of the probe head.

According to an embodiment of the probe of the present invention, it is preferable that an external thread for connection is formed on an outer circumference of the probe tail.

According to an embodiment of the probe of the present invention, it is preferable that a boss is provided on an outer circumference of the probe body at a rear portion thereof connected with the external thread, and an end face of the boss facing the probe head is smoothly transitioned toward the probe body, and an end face of the boss facing the probe tail is perpendicular to an axis of the probe and forms a stop surface for preventing the external thread from continuing to advance.

According to an embodiment of the probe of the present invention, it is preferable that a plurality of clamping faces for clamping the probe are provided on the boss.

According to an embodiment of the probe of the present invention, it is preferable that a plurality of vent holes are formed on the outer circumference of the probe.

According to an embodiment of the probe of the present invention, preferably, an inner wall of the outer conductive shell is shrunk toward a central line direction at a portion near the probe head and forms an inner step, and the insulating layer and the inner conductive rod pass through a central hole of the inner step.

According to an embodiment of the probe of the present invention, preferably, a plurality of tail anti-slip grooves for restricting movement of the insulating layer are formed on the inner wall of the outer conductive shell in the position adjacent to the probe tail.

According to an embodiment of the probe of the present invention, preferably, a plurality of head anti-slip grooves for restricting movement of the insulating layer are formed on a wall surface of the central hole of the inner step of the outer conductive shell in the position adjacent to the probe head.

Compared with the prior art, the embodiments of the present invention have the following advantages: the probe of the invention is simple in structure, convenient to use, simple in operation, of high reliability. The outer conductive shell and the inner conductive rod of the probe of the invention are both electrically conductive materials. An insulating material is filled between two conductive materials, which forms an electrode structure. By taking advantage of the characteristics that different organizations of a living body have different electrical features, if the probe according to one aspect of the invention is used to detect a body tissue and determine a type of the body tissue being detected based on different electrical signals fed back by different tissues, and in combination with bio-recognition-related hardware and software, it can avoid a medical accident in which a spinal cord or nerve is injured by a screw intruded into a vertebral foramen, improving surgical safety, reducing psychological pressure on both sides of doctors and patients, increasing success rate of surgery and reducing cost of surgery.

A second aspect of the present invention provides a method of manufacturing a probe according to the first aspect of the present invention, which comprises steps of:

S1, manufacturing an outer conductive shell of the probe of the first aspect of the present invention;

S2, manufacturing an inner conductive rod of the probe;

S3, performing a marking operation on the inner conductive rod manufactured in S2;

S4, cleaning the inner conductive rod and the outer conductive shell obtained in the above steps S1 to S3;

S5, heating the inner conductive rod and the outer conductive shell in an oven after having been cleaned;

S6, sheathing an insulating sleeve on the inner conductive rod obtained in S5;

S7, fitting the inner conductive rod sheathed with the insulating sleeve inside the outer conductive shell;

S8, mounting the outer conductive shell having the inner conductive rod therein obtained in S7 into an injection mold;

S9, mounting the injection mold onto an injection molding machine, and adjusting the position and the opening and closing state of the injection mold to ensure smooth opening and closing of the injection mold;

S10, cleaning the injection mold;

S11, pre-heating the injection mold having been cleaned;

S12, injection molding with an insulating material;

S13, cleaning a semi-finished probe after the injection molding;

S14, removing excess material of the outer conductive shell of the semi-finished probe obtained in S13 to obtain a final shape of the probe; and S15, performing a comprehensive performance detection on the probe obtained in S14.

According to the method of manufacturing the probe in an embodiment of the present invention, it is preferable that the inner conductive rod, the outer conductive shell, and the insulating material have a same thermal expansion property.

According to the method of manufacturing the probe in an embodiment of the present invention, it is preferable that the outer conductive shell in S1 and the inner conductive rod in S2 are made of a medical metal material.

According to the method of manufacturing the probe in an embodiment of the present invention, it is preferable that the insulating material is a medical insulating material.

According to the method of manufacturing the probe in an embodiment of the present invention, preferably, the marking operation in S3 is a laser marking operation.

According to the method of manufacturing the probe in an embodiment of the present invention, it is preferable that performing a comprehensive performance detection in S15 further comprises:

S151 performing an appearance detection;

S152 performing a mechanical property detection;

S153 performing an electrical performance detection.

According to the method of manufacturing the probe in an embodiment of the present invention, preferably, the method of manufacturing the probe further comprises a step of manufacturing an injection mold.

According to the method of manufacturing the probe in an embodiment of the present invention, preferably, the method of manufacturing the probe further comprises a step of manufacturing jig and fixture for holding and positioning the semi-finished probe in S14.

According to the method of manufacturing the probe in an embodiment of the present invention, preferably, when the outer conductive shell is manufactured in S1, a funnel-shaped injection port with a large opening facing outward is formed at a position of the probe head.

According to the method of manufacturing the probe in an embodiment of the present invention, it is preferable that a plurality of vent holes are formed on an outer surface of the probe body when the outer conductive shell is manufactured in S1.

According to the method of producing the probe in an embodiment of the present invention, preferably, in steps S4 and S10, the cleaning may be one of chemical cleaning or ultrasonic cleaning.

The method of manufacturing a probe according to the second aspect of the present invention is simple and easy, a manufacture cycle is short, a time cost is low, and a working efficiency is high. In the probe manufactured by the method of the present invention, a bonding force between the outer conductive shell and the insulating layer and between the insulating layer and the inner conductive rod are strong, so the components are not easy to fall off; the probe has excellent electrical properties, exquisite structure, good performance, low cost and is easy to use.

LIST OF REFERENCE NUMERALS 1-probe head; 2-probe body; 3-probe tail; 4-outer conductive shell; 5-inner conductive rod; 6-insulating layer; 7-external thread; 8-boss; 9-stop surface; 10-clamping face; 11-vent hole; 12-inner step; 13-tail anti-slip groove;14-head anti-slip groove; 15-injection port; 16-positioning groove.

DETAILED DESCRIPTION

Exemplary embodiments of the present disclosure will be described hereinafter clearly and completely with reference to accompanying drawings. Apparently, the embodiments described herein are only portions of embodiments of the disclosure, rather than all embodiments of the disclosure. It is intended that all other embodiments obtained by those skilled in the art according to the disclosed embodiments without inventive labor are within the scope of the present invention.

In the description of the present disclosure, it is to be noted that the terms of "center", "upper", "lower", "left", "right", "vertical", "horizontal", "internal", "external" and the like simply indicate orientational or positional relationship based on the accompanying drawings and are used only for the purpose of facilitating and simplifying the description of the invention, rather than specifying or implying that any device or elements indicated must have a certain orientation, constitute with a certain orientation, or operate in a certain orientation. Therefore, these terms will not be interpreted as limiting the present invention. Further, the terms of "first", "second" and "third" are only used for description purpose, rather than being interpreted as specifying or implying relative importance.

In the description of the present disclosure, it is to be noted that, unless otherwise specified or defined clearly, the term of "attach", "connect to", "connect with", "couple" and the like should be interpreted broadly. For example, they may refer to fixed connection, or detachable connection, or integral connection; they may refer to mechanical connection, or electrical connection; they may refer to direct connection, or indirect connection through an intermediate agent, or internal communication between two components. For those skilled in the art, specific meaning of these terms in the present disclosure may be understood in combination with specific situations or contexts.

In the following, the present invention will be further described in detail through specific embodiments in combination with the accompanying drawings.

Figure 1:
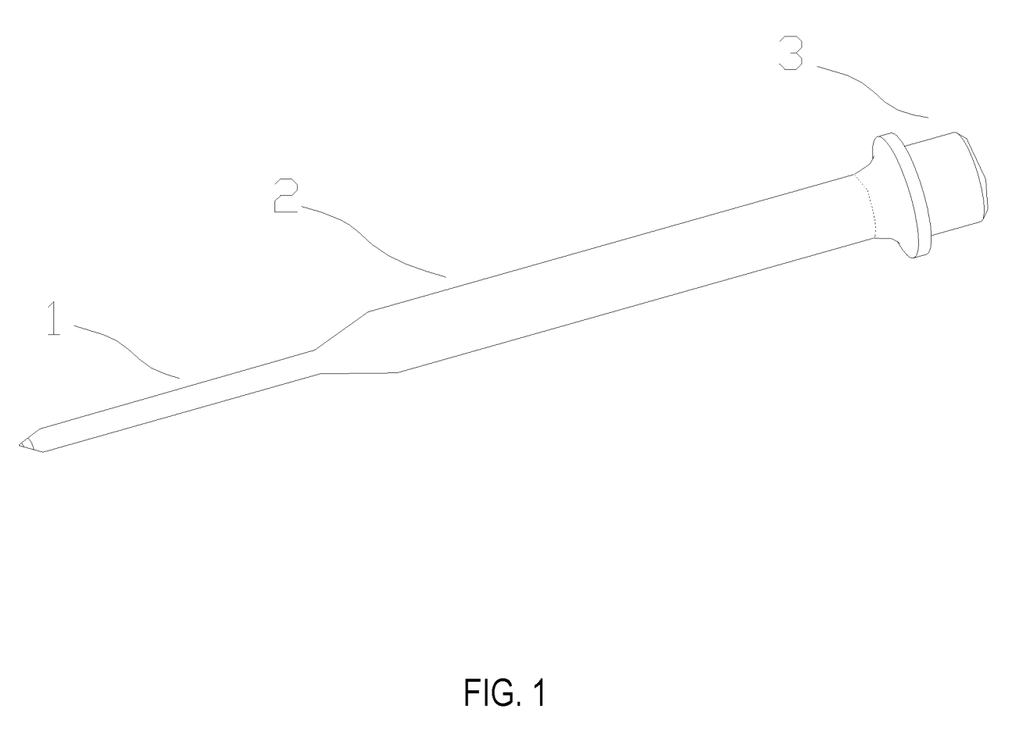
FIG. 1 is a perspective view according to an embodiment of a probe of the present invention.
Figure 2:
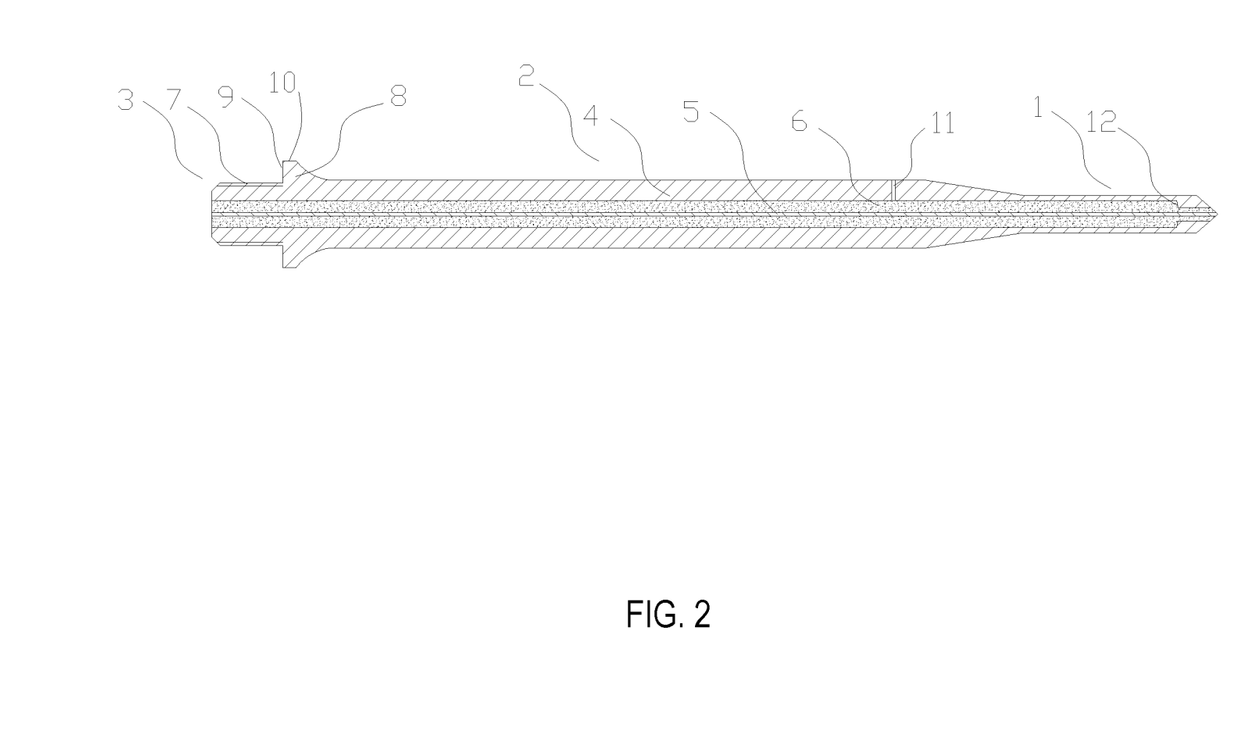
FIG. 2 is a schematic cross-sectional view showing an embodiment of a probe of the present invention.

As shown in FIG. 1 and FIG. 2, the probe of an embodiment of the present invention has a long cylindrical shape and includes a probe head 1, a probe body 2 located at the rear of the probe head 1, and a probe tail 3 located at the rear of the probe body 2. The probe is of a three-layer composite structure. An outermost layer of the probe is an outer conductive shell 4, an innermost layer of the probe is an inner conductive rod 5, and an insulating layer 6 is disposed between the outer conductive shell 4 and the inner conductive rod 5.

The probe of the present invention can replace the conventional opener to form bottom holes used for mounting screws in bones. The outer conductive shell 4 and the inner conductive rod 5 of the probe of the present invention are separated by an insulating layer 6, and an electrode structure can be formed between the inner and outer conductive materials. When the medical staff uses the probe bottom hole of the present invention, according to different characteristic signals generated by different body tissues contacted by the probe, the different tissue structures of the bottom hole can be discriminated, and the parameters such as the direction and angle of the surgical bottom hole can be regulated. Therefore, it can effectively prevent the conditions such as skew perforation, the perforation error, the excessive drilling, etc. which may injure the patient in a orthopedic surgery, thereby reduce the risk of surgery, improve the operation efficiency, and thereby reduce the psychological pressure of both doctors and patients.

Referring to FIG. 2, as an embodiment of the present invention, the outer diameter of the probe head 1 is smaller than the probe body 2, the outer surface of the probe head 1 is smoothly connected with the outer surface of the probe body 2, and the end of the probe head 1 has a conical structure. The inner conductive rod 5 protrudes from the end of the conical structure of the probe head 1 to form a metal tip. When the doctor uses the probe of the present invention to make a bottom hole in the bone, the external force applied by the doctor to the probe is concentrated on the metal of the probe. The tip, which is the tip of the inner conductive rod 5, creates a very large stress at a single point on the bone surface, and the hard bone layer on the bone surface can be easily broken. At the same time, the structure that the inner conductive rod 5 protrudes from the probe head 1, so that the inner and outer conductive materials are fully exposed in the body tissue, which is more advantageous for identifying the electrical characteristics of the body tissue.

In FIG. 2, the outer circumference of the probe tail 1 is provided with an external thread 7 for connection. Of course, depending on the needs of use, the connection mode of the probe to the host can be divided into a detachable connection and a fixed connection. The detachable connection is not limited to the external thread 7, and any connection structure capable of connecting the probe to the host machine in a detachable manner can be used for the detachable connection of the probe to the host machine. For example, an internal thread is provided on the tail 3 of the probe, and correspondingly, the connection portion of the host machine is an external thread structure. Alternatively, a snap-fit type fastener may be arranged on the probe tail 3, which will be rotated into a corresponding snap ring on a connection portion of the host machine for locking upon connection. Riveting, welding, gluing etc. can be adopted as the fixed connection method.

As an embodiment of the present invention, a boss 8 is provided on the outer circumference of a portion where the distal end of the probe body 2 is connected to the external thread of the probe tail 3.and the boss 8. An end face of the boss 8 facing the probe head 1 is connected with the probe body 2 in a smooth transition, and an end face of the boss 8 facing the probe tail 3 is perpendicular to an axis of the probe and forma a stop surface 9 for preventing the external thread from continuing to advance. Preferably, a plurality of clamping faces 10 for clamping the probe are arranged on the boss 8. When the probe is installed on a main machine, the probe can be screwed in by a common tool such as a wrench to prevent the probe from falling off accidentally.

Figure 3:
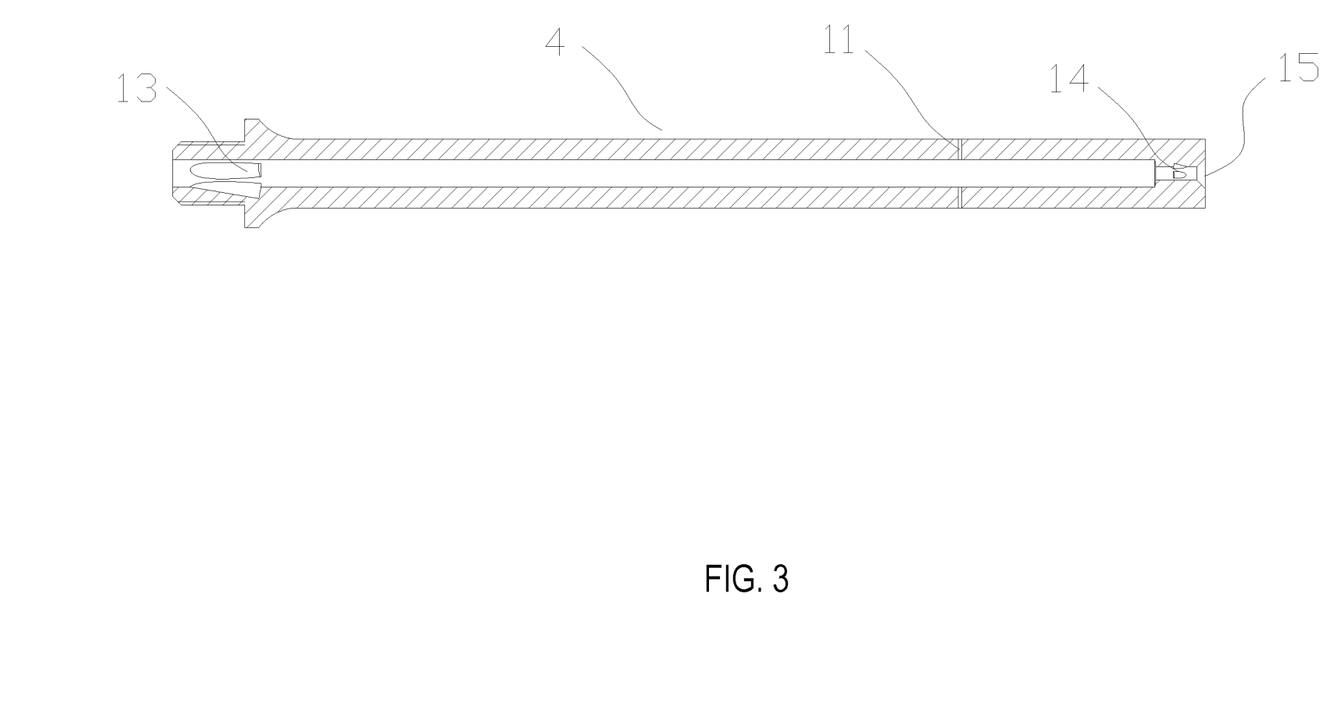
FIG. 3 is schematic cross-sectional view showing another embodiment of a probe of the present invention.

Referring to FIG. 3, as a preferred embodiment of the present invention, a plurality of venting holes 11 are formed on the outer circumference of the probe body 2. The venting holes 11 are arranged to satisfy a double-side feeding mode during injection molding. When an insulating material is injected into the outer conductive shell 4, the air in the inner cavity of the outer conductive shell 4 can be discharged from the vent holes 11, which effectively prevents the insulating material from being under-filled or generating bubbles due to presence of air thereby affecting insulation performance. Double-side feeding can also improve the efficiency of injection molding, saving time and labor costs. It is also possible to shorten the flow stroke of the injection molding material for the case of poor fluidity of the injection molding material, and to avoid the situation that the injection molding is not full and the rejection rate is high.

The venting holes 11 may be a circular hole, a square hole or of other irregular shape, and its axis may be various forms such as being perpendicular or inclined to the axis of the outer conductive shell 4. The venting holes 11 may be uniformly distributed or non-uniformly distributed along the outer surface of the outer conductive shell 4, and may be in one or more rows.

Referring again to FIG. 1, as an embodiment of the present invention, inside the probe, an inner wall of the outer conductive shell 4 is shrunk toward a central line direction at a positon near the probe head 1 to form an inner step 12. The insulating layer 6 and the inner conductive rod 5 passes through a central hole of the inner step 12. The arrangement of the inner step 12 maximizes the contact area between the insulating layer 6 and the outer conductive shell 4, so that an adhesion force between the insulating layer 6 and the outer conductive shell 4 after injection molding is greater than a force generated in operation. The central hole of the inner step 12 may be of, for example, a tapered structure with a large opening facing outward, and the cross section thereof may be various regular or irregular shapes. A thickness of the insulating layer 6 in the central hole of the inner step 12 is smaller than a thickness of the insulating layer 6 outside the central hole, so that an exposed area of the insulating layer 6 at the end of the probe head 1 is small, and a stressed area in contact with a body tissue during operation is also small, which can effectively prevent the material of the insulating layer 6 from being broken, and further improve safety in use and sensitivity of the probe.

As shown in FIG. 3, in the embodiment of the present invention, a plurality of tail anti-slip grooves 13 for restricting movement of the insulating layer 6 may be formed on the inner wall of the outer conductive shell 4 adjacent to the probe tail 3. Alternatively, a plurality of head anti-slip grooves 14 for restricting movement of the insulating layer 6 may be formed on a wall surface of the central hole of the inner step 12 of the outer conductive shell 4 adjacent to the probe head 1. The arrangement of the tail anti-slip grooves 13 and the head anti-slip grooves 14 can effectively prevent the insulating layer 6 from moving and rotating as a whole, and increase the contact area between the insulating layer 6 and the outer conductive shell 4, thereby improving the bonding strength between the two. Preferably, an inclination angle of the tail anti-slip grooves 13 and the head anti-slip grooves 14 is 5 to 85 degrees. The tail anti-slip groove 13 and the head anti-slip groove 14 can be machined with a process such as an internal thread process or a knurling process. It is also possible to form various regular or irregular projections or recesses on the inner wall of the outer conductive shell 4.

Compared with the prior art, the embodiments of the present invention have the following advantages: the probe is simple in structure, convenient to use, simple in operation, of high reliability. Since the outer conductive shell 4 and the inner conductive rod 5 of the probe of the invention are both electrically conductive materials, when an insulating material is filled between two conductive materials, an electrode structure is formed. By utilizing the advantage of the characteristics that different organizations of a living body have different electrical features, if the probe according to one aspect of the invention is used in combination with bio-recognition-related hardware and software, the body tissue type detected by the probe can be known. Thereby it can avoid a medical accident in which a spinal cord or nerve is injured by a screw intruded into a vertebral foramen, improving surgical safety, reducing psychological pressure on both sides of doctors and patients, increasing success rate of surgery and reducing cost of surgery.

Figure 5:
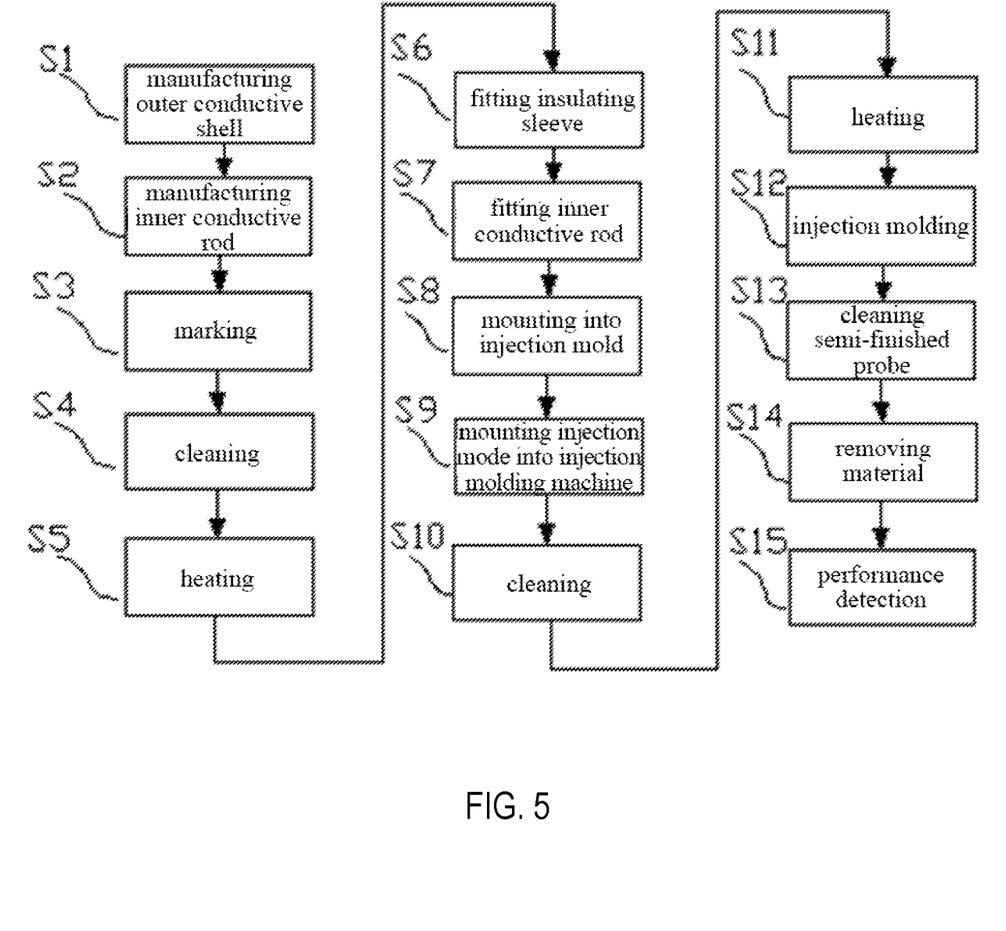
FIG. 5 is a flow chart showing an embodiment of a method of manufacturing a probe of the present invention.

Another aspect of the invention provides a method of making a probe. FIG. 5 is a flow chart showing a method of manufacturing the probe in an embodiment of the present invention. As shown in FIG. 5, the method of manufacturing a probe comprises the following steps:

S1, manufacturing an outer conductive shell of the probe;

S2, manufacturing an inner conductive rod of the probe;

S3, performing marking operation on the inner conductive rod manufactured in S2;

S4, cleaning the inner conductive rod and the outer conductive shell obtained in the above steps S1 to S3;

S5, heating the inner conductive rod and the outer conductive shell in an oven after being cleaned;

S6, sheathing an insulating sleeve on the inner conductive rod obtained in the above S5;

S7, fitting the inner conductive rod sheathed with the insulating sleeve inside the outer conductive shell;

S8, mounting the outer conductive shell having the inner conductive rod therein obtained in S7 into an injection mold;

S9, mounting the injection mold onto an injection molding machine, and adjusting the position and the opening and closing state of the injection mold to ensure smooth opening and closing of the injection mold;

S10, cleaning the injection mold;

S11, pre-heating the injection mold having been cleaned;

S12, injection molding with an insulating material;

S13, cleaning a semi-finished probe after the injection molding;

S14, removing excess material of the outer conductive shell of the semi-finished probe obtained in S13 to obtain a final shape of the probe; and S15, performing a comprehensive performance detection on the probe obtained in S14.

In the probe manufacturing method of an embodiment of the present invention, when the outer conductive shell 4 is machined and manufactured, various machining methods can be used for cutting and shaping, such as high-pressure deep hole drilling, axial small cutting depth fast feeding high-speed milling, thereby realizing minor deformation of a head portion and an inner cavity of outer conductive shell 4.

In the probe manufacturing method of an embodiment of the present invention, the inner conductive rod 5, the outer conductive shell 4, and the insulating material have same thermal expansion properties. The same thermal expansion properties can prevent separation of the insulating material from the inner conductive rod 5 or the outer conductive shell 4 during a heating or cooling process of the inner conductive rod 5, the outer conductive shell 4 and the insulating material thereby affecting the performance of the probe. During the filling process of the insulating material, an existing insulating pipe can be sleeved around the outer circumference of the inner conductive rod 5, and the two can be nested in the inner cavity of the outer conductive shell 4. In this way, the existing insulating pipe can serve to support the inner conductive rod 5, effectively reducing requirement for straightness of the inner conductive rod 5 and greatly reducing the probability of short-circuit thereof. The material of the existing insulating pipe is consistent with the filling insulating material, and the inner and outer diameters thereof respectively clearance-fitted with the outer conductive shell 4 and the inner conductive rod 5.

In the probe manufacturing method of an embodiment of the present invention, it is preferable that the outer conductive shell 4 in S1 and the inner conductive rod 5 in S2 are made of a medical metal material to meet the criteria of medical devices. The insulating material is medical insulating material to meet criteria of medical devices.

The marking operation in S3 may be a laser marking operation, which is simple, of high efficiency and low cost.

Figure 6:
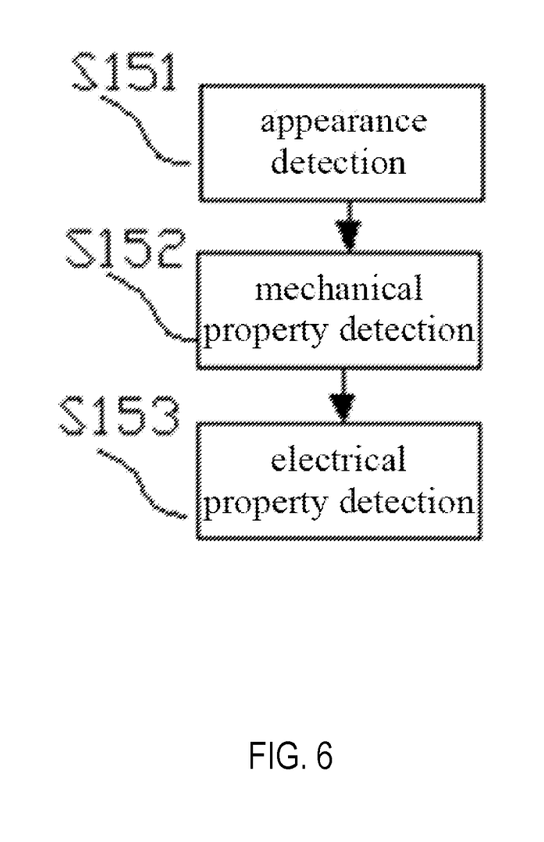
FIG. 6 is a flow chart showing a detecting method according to another embodiment of a method of manufacturing a probe of the present invention.

As a preferred embodiment of the present invention, the step of performing a comprehensive performance detection in S15 further includes:

S151, performing an appearance detection, including detection of bonding surface in injection molding at the end face, whether the intermediate vent holes 11 have the discharge of the insulating material, and other conventional inspections;

S152, performing a mechanical property detection, mainly involving using a destructive test to detect the strength of the outer conductive shell 4, the inner conductive rod 5, and the insulating layer 6;

S153, performing an electrical performance detection, mainly involving using a dedicated detecting tool to detect the electrical performance between the outer conductive shell 4 and the inner conductive rod 5 in a plurality of states including a direct current state and an alternating current state so as to ensure the stable performance thereof.

Figure 4A:
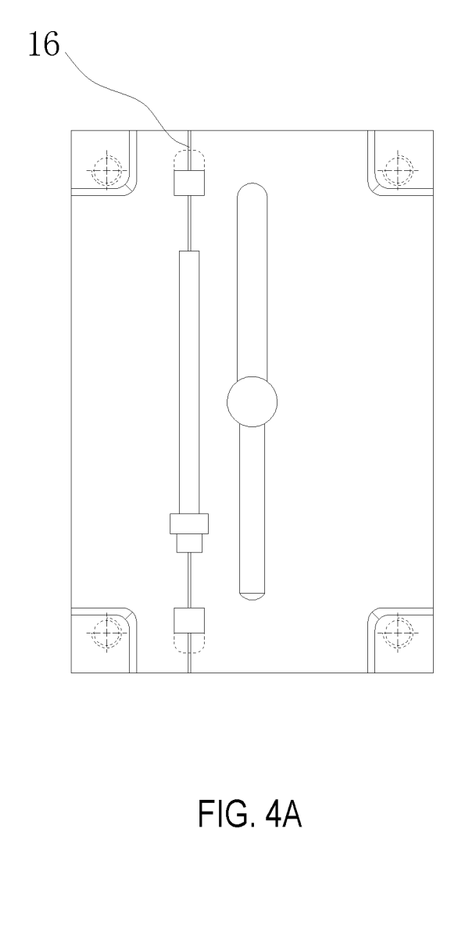
FIG. 4A is a schematic view of an upper injection mold according to an embodiment of a probe of the present invention.
Figure 4B:
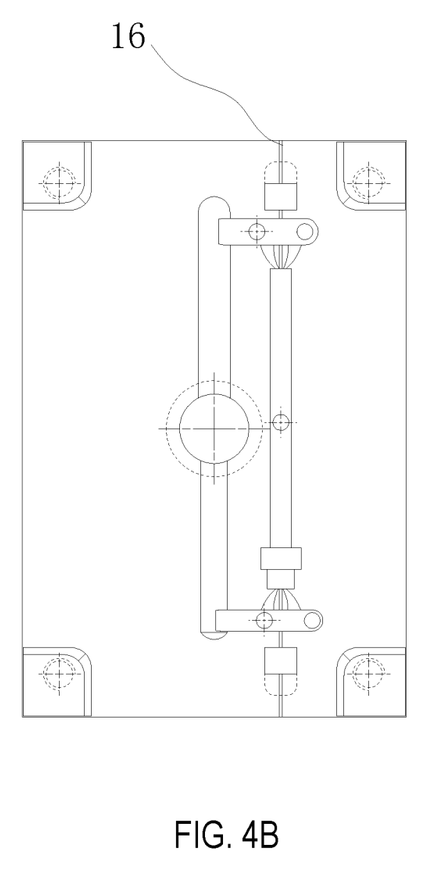
FIG. 4B is a schematic view of a lower injection mold according to an embodiment of a probe of the present invention.

Referring to FIGS. 4A-4B, as a preferred embodiment of the present invention, the method of making a probe further includes a step of manufacturing an injection mold. An upper injection mold and a lower injection mold employ positioning grooves 16 matching the diameter of the inner conductive rod 5 at both ends of the upper injection mold and the lower injection mold for accurately positioning the inner conductive rod 5 in the radial direction and compressing and fixing the inner conductive rod when the upper and lower injection molds are closed, so that the inner conductive rod 5 does not move during the injection molding process, and a short circuit due to displacement and severe deformation can be avoided. Further, the upper and lower injection molds are provided with positioning and clamping surfaces corresponding to that of the outer conductive shell 4, thereby ensuring that the outer conductive shell 4 does not displace during the injection molding process. Other aspects of the upper and lower injection molds are similar to ordinary injection molds.

In the method of manufacturing a probe according to an embodiment of the present invention, a step of manufacturing a jig and fixture for clamping and positioning the semi-finished probe in step S13 may be further included. When the excess material of the outer conductive shell 4 of the semi-finished probe obtained in step S12 is removed to obtain a final shape of the probe, a special jig and fixture is necessary to meet the requirement of positioning accuracy. An axial high-precision unsealed sleeve or a special raised chuck can be used to position it and its accuracy is within a range of designed tolerance.

Referring to FIG. 3, in the method of manufacturing a probe according to an embodiment of the present invention, when the outer conductive shell 4 is manufactured in step S1, a funnel-shaped injection port 15 having a large opening facing outward can be provided at a position of the probe head 1 to facilitate injection of the injection material into the inner cavity of the outer conductive shell 4.

In the method of manufacturing a probe according to an embodiment of the present invention, when the outer conductive shell 4 is manufactured in step S1, a plurality of vent holes 11 are formed on an outer surface of the probe body. The vent holes 11 may be provided in the middle of the probe head 1 or on the circumference of the outer conductive shell 4 near the inner step 12. The arrangement of the venting holes 11 can satisfy a double-side feeding mode during injection molding. When an insulating material is injected into the outer conductive shell 4, the air in the inner cavity of the outer conductive shell 4 can be discharged from the vent holes 11, which effectively prevents the insulating material from being under-filled or generating bubbles due to presence of air, thereby affecting insulation performance. Double-side feeding can also improve the efficiency of injection molding, saving time and labor costs. It is also possible to shorten the flow stroke of the injection molding material for the case of poor fluidity of the injection molding material, and to avoid the situation that the injection molding is not full and the rejection rate is high.

The cleaning method in S4 and S10 may be one of chemical cleaning or ultrasonic cleaning. Chemical cleaning or ultrasonic cleaning are common methods for cleaning stains on mechanical parts, and have high cleaning efficiency and a thorough cleaning can be made.

In the method of manufacturing a probe according to the present invention, the respective steps are clear and reasonable, the process is simple and easy, the manufacture cycle is short, the time cost is low, and the work efficiency is high. The bonding force between the outer conductive shell and the insulating layer and between the insulating layer and the inner conductive rod of the probe manufactured by the method of the present invention are strong, the inner conductive rod is not easy to fall off, and the electrical properties are excellent. The probe has an exquisite structure, excellent performance, low cost and is easy to use.

Finally, it should be noted that the above embodiments are merely illustrative of the technical solutions of the present invention, and are not intended to be limiting; although the present invention has been described in detail with reference to the foregoing embodiments, those skilled in the art will understand that the technical solutions described in the foregoing embodiments may be modified, or some or all of the technical features may be equivalently substituted; and the modifications or substitutions do not make the spirit of associated solutions deviate from the scope of the technical solutions of the embodiments of the present invention.

What is claimed is:

1. A method of manufacturing a probe, comprising steps of:
   S1, manufacturing an outer conductive shell;
   S2, manufacturing an inner conductive rod;
   S3, performing a marking operation on the inner conductive rod manufactured in S2;
   S4, cleaning the inner conductive rod and the outer conductive shell obtained in the above step S3;
   S5, heating the inner conductive rod and the outer conductive shell in an oven after having been cleaned;
   S6, sheathing an insulating sleeve on the inner conductive rod obtained in S5;
   S7, fitting the inner conductive rod sheathed with the insulating sleeve inside the outer conductive shell;
   S8, mounting the outer conductive shell having the inner conductive rod therein obtained in S7 into an injection mold;
   S9, mounting the injection mold onto an injection molding machine, and adjusting the position and the opening and closing state of the injection mold to ensure smooth opening and closing of the injection mold;
   S10, cleaning the injection mold;
   S11, pre-heating the injection mold having been cleaned;
   S12, injection molding with an insulating material;
   S13, cleaning a semi-finished probe after the injection molding;
   S14, removing excess material of the outer conductive shell of the semi finished probe obtained in S13 to obtain a final shape of the probe; and
   S15, performing a comprehensive performance detection on the probe obtained in S14.

2. The method according to claim 1, wherein
   the inner conductive rod, the outer conductive shell, and the insulating material have a same thermal expansion property.

3. The method according to claim 1, wherein
   the outer conductive shell in S1 and the inner conductive rod in S2 are made of a medical metal material.

4. The method according to claim 1, wherein
   the insulating material is a medical insulating material.

5. The method according to claim 1, wherein
   the marking operation in S3 is a laser marking operation.

6. The method according to claim 1, wherein
performing a comprehensive performance detection in S15 further comprises:
S151, performing an appearance detection;
S152, performing a mechanical property detection;
S153, performing an electrical performance detection.

7. The method according to claim 1, further comprising a step of manufacturing the injection mold.

8. The method according to claim 1, further comprising a step of manufacturing jig and fixture for holding and positioning the semi-finished probe in S14.

9. The method according to claim 1, wherein
when the outer conductive shell is manufactured in S1, a funnel-shaped injection port with a large opening facing outward is formed at a position of the probe head.

10. The method according to claim 1, wherein
a plurality of vent holes are formed on an outer surface of the probe body when the outer conductive shell is manufactured in S1.

11. The method according to claim 1, wherein
in steps S4 and S10, the cleaning may be one of chemical cleaning or ultrasonic cleaning.

\* \* \* \* \*